(12) United States Patent
Vu et al.

(10) Patent No.: US 8,396,796 B1
(45) Date of Patent: Mar. 12, 2013

(54) METHOD AND SYSTEM FOR ESTABLISHING A HEALTHCARE NETWORK ACROSS SMALL BUSINESSES

(75) Inventors: Miriam Nga-Shun Vu, San Francisco, CA (US); Lucinda Foss, San Francisco, CA (US)

(73) Assignee: Intuit Inc., Mounain View, CA (US)

( * ) Notice: Subject to any disclaimer, the term of this patent is extended or adjusted under 35 U.S.C. 154(b) by 569 days.

(21) Appl. No.: 12/323,806

(22) Filed: Nov. 26, 2008

(51) Int. Cl.
*G06Q 40/00* (2012.01)
(52) U.S. Cl. ............................................. 705/40; 705/2
(58) Field of Classification Search ........... 705/2, 25–45
See application file for complete search history.

(56) References Cited

U.S. PATENT DOCUMENTS

| | | | | |
|---|---|---|---|---|
| 2002/0091550 | A1* | 7/2002 | White et al. | 705/4 |
| 2003/0097281 | A1* | 5/2003 | Momose | 705/4 |
| 2005/0055299 | A1* | 3/2005 | Chambers et al. | 705/36 |
| 2009/0171831 | A1* | 7/2009 | Johnson et al. | 705/37 |
| 2009/0171854 | A1* | 7/2009 | Joseph et al. | 705/80 |

* cited by examiner

*Primary Examiner* — Gregory Pollock
*Assistant Examiner* — Jennifer Liu
(74) *Attorney, Agent, or Firm* — McKay and Hodgson, LLP; Philip McKay; Sean P. Lewis

(57) ABSTRACT

A system and method for establishing a healthcare network across small businesses whereby two or more small businesses and one or more healthcare insurance providers are enrolled in a small business employee healthcare network. The one or more healthcare insurance providers then offer one or more healthcare insurance plans through the small business employee healthcare network at initial bid prices. Employees of the enrolled small businesses are then provided an opportunity to view the one or more healthcare insurance plan offers. Interested employees of the enrolled small businesses then opt into one or more of the one or more healthcare insurance plan offers through the small business employee healthcare network. As the number, and/or the profile, of the employees that opt into a given one of the one or more healthcare insurance plan offers increases and/or changes, and/or in response to bids from enrolled competitor healthcare insurance providers, the one or more healthcare insurance providers can change the bid prices for the one or more healthcare insurance plan offers. After a specified time period, the healthcare insurance provider having offered the lowest bid is contracted to provide the one or more healthcare insurance plans, at the lowest bid price, to the employees that opted in.

4 Claims, 3 Drawing Sheets

METHOD AND SYSTEM FOR ESTABLISHING A HEALTHCARE NETWORK ACROSS SMALL BUSINESSES

BACKGROUND

The cost of healthcare continues to be a significant problem in the United States. For over a decade healthcare costs have been increasing at a rate considerably above that of inflation. With a significant percentage of the United States population being over 40, i.e. the baby-boomers and the generation Xers, there is little doubt in anyone's mind that this trend will continue in the foreseeable future.

According to the annual "Survey of Employer Health Benefits," a report released by the Henry J. Kaiser Family Foundation and the Health Research and Educational Trust, healthcare costs in the United States rose 7.7 percent between spring 2005 and spring 2006. While this increase was the smallest in seven years, the rates still surged twice as fast as the overall inflation of worker wages. Currently, 16 percent of the United States gross domestic product goes toward healthcare spending, and experts predict that that number will climb to 25 percent by 2030, according to Julius A. Karash's September 27 editorial in The Kansas City Star. Additionally, the number of uninsured people climbed by 1.3 million, bringing the total number of uninsured in the U.S. to 46.6 million.

Given this situation, more and more employees, and/or potential employees, are insisting that healthcare insurance programs be part of their compensation package. Consequently, it is becoming more and more evident that if employers wish to retain their current employees, and/or hire new employees, they must offer some form of health insurance as part of their employee benefit package and, in many cases, the better the health insurance program offered, the better chance the employer has of keeping key employees, and/or hiring the best new employees. In addition, some States now require that employers offer some form of health insurance to their employees and many more States are considering such legislation, as is the Federal Government.

However, for many small businesses, and employees of small businesses, healthcare insurance programs that have reasonably desirable benefits are extremely hard to obtain and, if obtainable, are often so costly that they are not economically viable for either the small business employer or the small business employee. The main reason healthcare insurance is so difficult to obtain and/or expensive for small businesses in particular is that with a limited number of employees, the healthcare insurance providers can't spread their exposure over large numbers of employees, and correspondingly large numbers of premium payments.

As an example, if a small business has five employees, then from the healthcare insurance provider's perspective, there is considerable risk in offering the small business employees heath insurance. This is because if any one of the five employees, i.e., 20 percent of the business's work force, becomes even moderately ill, or incurs even a modest injury, the cost of paying that one employee's medical bills can easily exceed several years of premiums collected by the healthcare insurance provider for all five of the small business's employees. In addition, in the period of time it takes to recoup these costs, it is quite possible yet another employee will take ill or be injured, thereby further increasing the losses carried by the healthcare insurance provider. Consequently, in light of this risk, the healthcare insurance provider either will not offer healthcare insurance to the small business, or if it is offered, as some States require by law, the healthcare insurance is offered at a very high cost to offset the risk.

In contrast, large businesses have numerous employees, and numerous potential premiums for those employees. Consequently, from the healthcare insurance provider's perspective, there is significantly less risk in offering the large business employees health insurance. This is because it is statistically less likely that 20 percent of a large business's employees will be ill, or injured, in the same time frame and if any one, or a small percentage, of the numerous employees becomes even seriously ill, or incurs even a serious injury, the cost of paying the employee's, or employees', medical bills can be easily offset by even modest premiums collected by the healthcare insurance provider for all of the large business's numerous employees. Consequently, in light of this reduced risk, the healthcare insurance providers actively court large businesses and often offer their employees healthcare insurance at significant volume discounts. Indeed, large businesses are so desirable to healthcare insurance providers, and the discounts offered are often so significant, that many large businesses can, and do, offer their employees the choice of multiple healthcare insurance programs, often from multiple healthcare insurance providers.

At the time of filing, it is reported that over 50 percent of all United States Citizens employed in the private sector are employed by small businesses.

Consequently, the inability of small businesses to obtain adequate healthcare insurance programs for their employees at a reasonable cost is truly a national problem and leaves literally tens of millions of people without adequate healthcare insurance coverage each year.

SUMMARY

In accordance with one embodiment, a system and method for establishing a healthcare network across small businesses includes a process for establishing a healthcare network across small businesses whereby, in one embodiment, two or more small businesses and one or more healthcare insurance providers are enrolled in a small business employee healthcare network. In one embodiment, the one or more healthcare insurance providers then offer one or more healthcare insurance plans through the small business employee healthcare network at initial, or current minimum, bid prices. Employees of the enrolled small businesses are then provided an opportunity to view the one or more healthcare insurance plan offers. In one embodiment, interested employees of the enrolled small businesses then opt into one or more of the one or more healthcare insurance plan offers through the small business employee healthcare network. In one embodiment, as the number, and/or the profile, of the employees that opt into a given one of the one or more healthcare insurance plan offers increases and/or changes, and/or in response to bids from enrolled competitor healthcare insurance providers, the one or more healthcare insurance providers can change the bid prices for the one or more healthcare insurance plan offers. In one embodiment, after a specified time period, the healthcare insurance provider having offered the lowest bid is contracted to provide the one or more healthcare insurance plans, at the lowest bid price, to the employees that opted in.

In one embodiment, participation in a small business employee healthcare network is offered to two or more small businesses and one or more healthcare insurance providers.

In one embodiment, two or more small businesses enroll in the small business employee healthcare network and agree to abide by provided small business terms associated with the small business employee healthcare network.

In one embodiment, the small business terms associated with the small business employee healthcare network are contractual in nature and set forth the obligations, rights, payment terms, and default remedies associated with small businesses enrolled in the small business employee healthcare network.

In one embodiment, one or more healthcare insurance providers enroll in the small business employee healthcare network and agree to abide by healthcare service provider terms associated with the small business employee healthcare network.

In one embodiment, the healthcare insurance provider terms associated with the small business employee healthcare network are contractual in nature and set forth the obligations, rights, payment terms, and default remedies associated with healthcare insurance providers enrolled in the small business employee healthcare network.

In one embodiment, the one or more enrolled healthcare insurance providers are then provided the opportunity and capability to offer one or more healthcare insurance plans to the employees of the two or more enrolled small businesses, in one embodiment, through an employee portal, such as an employee website maintained by the process for establishing a healthcare network across small businesses.

In one embodiment, the one or more enrolled healthcare insurance providers are provided the opportunity and capability to offer one or more healthcare insurance plans to the employees of the two or more enrolled small businesses through an employee website and/or database maintained by the small business employer. In one embodiment, the employee website is the same website used by employees to track their pay records, accumulated vacation time, sick days, and other payroll related data.

In one embodiment, the one or more enrolled healthcare insurance providers are provided the opportunity and capability to offer one or more healthcare insurance plans to the employees of the two or more enrolled small businesses on a periodic basis, such as an annual or semi annual basis, and/or with new employee packages, or as part of new employee processing.

In one embodiment, the one or more enrolled healthcare insurance providers are provided the opportunity and capability to offer one or more healthcare insurance plans to the employees of the two or more enrolled small businesses through any database, computing system, and/or a server system, or any web-site or other web-based system, and/or using a computer program product as discussed herein.

In one embodiment, the one or more enrolled healthcare insurance providers are provided the opportunity and capability to offer one or more healthcare insurance plans to the employees of the two or more enrolled small businesses via the Internet.

In one embodiment, the one or more enrolled healthcare insurance providers are provided the opportunity and capability to offer one or more healthcare insurance plans to the employees of the two or more enrolled small businesses through any network of computing systems and/or server systems that is comprised of multiple different computers, wireless devices, cellular telephones, digital telephones, two-way pagers, personal digital assistants, server computers, or any desired combination of these devices, that are interconnected using a network.

In one embodiment, the one or more enrolled healthcare insurance providers are provided the opportunity and capability to offer one or more healthcare insurance plans to the employees of the two or more enrolled small businesses through e-mail or through text messaging.

In one embodiment, the one or more enrolled healthcare insurance providers are provided the opportunity and capability to offer one or more healthcare insurance plans to the employees of the two or more enrolled small businesses through traditional postal and/or phone service.

In one embodiment, the one or more enrolled healthcare insurance providers are provided the opportunity and capability to offer one or more healthcare insurance plans to the employees of the two or more enrolled small businesses using any method, apparatus, process or mechanism for obtaining data, and/or for transferring data, images, screen displays, and/or text from one or more devices, computing systems, server systems, databases, web site/web functions and/or any systems to one or more other devices, computing systems, server systems, databases, web site/web functions and/or any systems, whether known at the time of filing or as thereafter developed.

In one embodiment, the one or more enrolled healthcare insurance providers are provided the opportunity and capability to offer one or more healthcare insurance plans to the employees of the two or more enrolled small businesses at an opening bid price that can be changed by the one or more enrolled healthcare insurance providers as data is collected regarding the number, and/or type, of employees opting into a given healthcare insurance plan.

In one embodiment, the one or more enrolled healthcare insurance providers are provided the opportunity and capability to offer one or more healthcare insurance plans to the employees of the two or more enrolled small businesses under opening, or initial, bid conditions such as, but not limited to, deductible amounts, percentages of medical costs covered, treatments covered, yearly cost caps, co-payments, etc. In one embodiment, the initial bid conditions can be changed by the one or more enrolled healthcare insurance providers as data is collected regarding the number and type of employees opting into a given healthcare insurance plan.

In one embodiment, a specified time period is designated during which employees of the two or more enrolled small businesses can opt into one or more of the one or more healthcare insurance plans offered by the one or more enrolled healthcare insurance providers.

In one embodiment, the specified time period is an open enrollment period established by the healthcare insurance providers, and/or the small business employers, and/or the process for establishing a healthcare network across small businesses. In one embodiment, the open enrollment period is set based on the period required to attain a threshold number of new potential employees to opt into the one or more healthcare insurance plans. In one embodiment, the open enrollment period is variable and varies according to when a threshold number of new employees opt into the one or more healthcare insurance plans.

In one embodiment, employees of the two or more enrolled small businesses can view the provisions and/or conditions of, and/or opt into, one or more of the one or more healthcare insurance plans offered by the one or more enrolled healthcare insurance providers through an employee portal, such as an employee website maintained by the process for establishing a healthcare network across small businesses.

In one embodiment, employees of the two or more enrolled small businesses can view the provisions and/or conditions of, and/or opt into, one or more of the one or more healthcare insurance plans offered by the one or more enrolled healthcare insurance providers through an employee website and/or database maintained by the small business employer. In one embodiment, the employee website is the same website used by employees to track their pay records, accumulated vacation time, sick days, and other payroll related data.

In one embodiment, employees of the two or more enrolled small businesses can view the provisions and/or conditions of, and/or opt into, one or more of the one or more healthcare insurance plans offered by the one or more enrolled healthcare insurance providers on a periodic basis, such as an annual or semi annual basis, and/or with new employee packages, or as part of new employee processing.

In one embodiment, employees of the two or more enrolled small businesses can view the provisions and/or conditions of, and/or opt into, one or more of the one or more healthcare insurance plans offered by the one or more enrolled healthcare insurance providers through any database, computing system, and/or a server system, or any web-site or other web-based system, and/or using a computer program product as discussed herein.

In one embodiment, employees of the two or more enrolled small businesses can view the provisions and/or conditions of, and/or opt into, one or more of the one or more healthcare insurance plans offered by the one or more enrolled healthcare insurance providers through any Internet connection.

In one embodiment, employees of the two or more enrolled small businesses can view the provisions and/or conditions of, and/or opt into, one or more of the one or more healthcare insurance plans offered by the one or more enrolled healthcare insurance providers through any network of computing systems and/or server systems that is comprised of multiple different computers, wireless devices, cellular telephones, digital telephones, two-way pagers, personal digital assistants, server computers, or any desired combination of these devices, that are interconnected using a network.

In one embodiment, employees of the two or more enrolled small businesses can view the provisions and/or conditions of, and/or opt into, one or more of the one or more healthcare insurance plans offered by the one or more enrolled healthcare insurance providers through e-mail or through text messaging.

In one embodiment, employees of the two or more enrolled small businesses can view the provisions and/or conditions of, and/or opt into, one or more of the one or more healthcare insurance plans offered by the one or more enrolled healthcare insurance providers through traditional postal and/or phone service.

In one embodiment, employees of the two or more enrolled small businesses can view the provisions and/or conditions of, and/or opt into, one or more of the one or more healthcare insurance plans offered by the one or more enrolled healthcare insurance providers through any method, apparatus, process or mechanism for obtaining data, and/or for transferring data, images, screen displays, and/or text from one or more devices, computing systems, server systems, databases, web site/web functions and/or any systems to one or more other devices, computing systems, server systems, databases, web site/web functions and/or any systems, whether known at the time of filing or as thereafter developed.

In one embodiment, employees of the two or more enrolled small businesses that opt into one or more of the one or more healthcare insurance plans offered by the one or more enrolled healthcare insurance providers are committed to accept the one or more healthcare insurance plans offered by the one or more enrolled healthcare insurance providers they opt into as long as the price of the one or more healthcare insurance plans remains at the opt in price, or lower.

In other embodiments, employees of the two or more enrolled small businesses that opt into one or more of the one or more healthcare insurance plans offered by the one or more enrolled healthcare insurance providers are committed to accept one or more healthcare insurance plans offered by the one or more enrolled healthcare insurance providers they opt into only if they remain opted into the one or more healthcare insurance plans offered by the one or more enrolled healthcare insurance providers at the end of the specified time period during which employees of the two or more enrolled small businesses can opt into one or more of the one or more healthcare insurance plans offered by the one or more enrolled healthcare insurance providers, and only as long as the final price of the one or more healthcare insurance plans is in a specified range.

As noted above, in one embodiment, during the specified time period, the one or more enrolled healthcare insurance providers can change the bid price for the one or more healthcare insurance plans offered and/or the bid conditions as discussed above. As also noted above, in one embodiment, the one or more enrolled healthcare insurance providers can change the bid price for the one or more healthcare insurance plans offered and/or the bid conditions based, at least in part, on the number of employees of the two or more enrolled small businesses that opt into the one or more healthcare insurance plans. In addition, in one embodiment, the one or more enrolled healthcare insurance providers may change the bid price for the one or more healthcare insurance plans offered, and/or the bid conditions, based, at least in part, in a competitive response to bid prices and/or the bid conditions offered by other enrolled healthcare insurance providers.

In one embodiment, at the end of the specified time period, the healthcare insurance provider having offered the lowest bid, and/or most favorable bid conditions, is contracted to provide the one or more healthcare insurance plans to the employees of the two or more enrolled small businesses that opted into the one or more healthcare insurance plans at the lowest bid price, and under the stated bid conditions.

In one embodiment, the two or more enrolled small businesses keep records of what employees are in which one of the one or more healthcare insurance plans offered and accepted. In one embodiment, the two or more enrolled small businesses use the records to deduct the proper amounts from a given employees pay to cover the employee's share of the one or more healthcare insurance plans opted into by the employee. In one embodiment, the deducted amounts, along with the small business employer's contribution, are aggregated for all employees having opted into the one or more healthcare insurance plans and premium payments are made as a lump sum to the healthcare insurance provider each pay period, or as contracted/stipulated in the small business employee healthcare network terms. In one embodiment, the records and payments are collected, kept, and, made using one or more computing system implemented data management systems.

In one embodiment, rather than providing individual employees of enrolled small businesses the ability to opt into the one or more healthcare insurance plans, the small businesses are grouped together and a specified percentage of each of the small businesses employee base are committed by the small business employer to take part in any of the one or more healthcare insurance plans the group of small businesses opts into. In this way, the small business employer acts as an agent for the small business employees. This embodiment is particularly useful when the small business employer is paying a large part of, or all of, the healthcare insurance plan premiums for the employees.

Using one or more embodiments of a system and method for establishing healthcare networks across small businesses, as disclosed herein, the employees of multiple enrolled small businesses are grouped together to increase the number of plan participants.

Consequently, by their increased numbers, the risk to the healthcare insurance provider is spread over a greater premium base and the collective bargaining power of the employees of the multiple enrolled small businesses allows them to potentially be offered discounts that previously were only available to employees of large companies. In addition, from the healthcare insurance provider's perspective, the actual number of employees of the multiple enrolled small businesses that opt into a given healthcare insurance plan is known in advance. As a result, using one or more embodiments of a system and method for establishing healthcare networks across small businesses, as disclosed herein, discounts can be offered based on real data and a known premium base.

Consequently, using one or more embodiments of a system and method for establishing healthcare networks across small businesses, as disclosed herein, employees of small businesses, small businesses, healthcare insurance providers, and, arguably, society as a whole, are all benefited.

In addition, as discussed in more detail below, using the below embodiments, with little or no modification and/or user input, there is considerable flexibility, adaptability, and opportunity for customization to meet the specific needs of various users under numerous circumstances.

Figure 1:
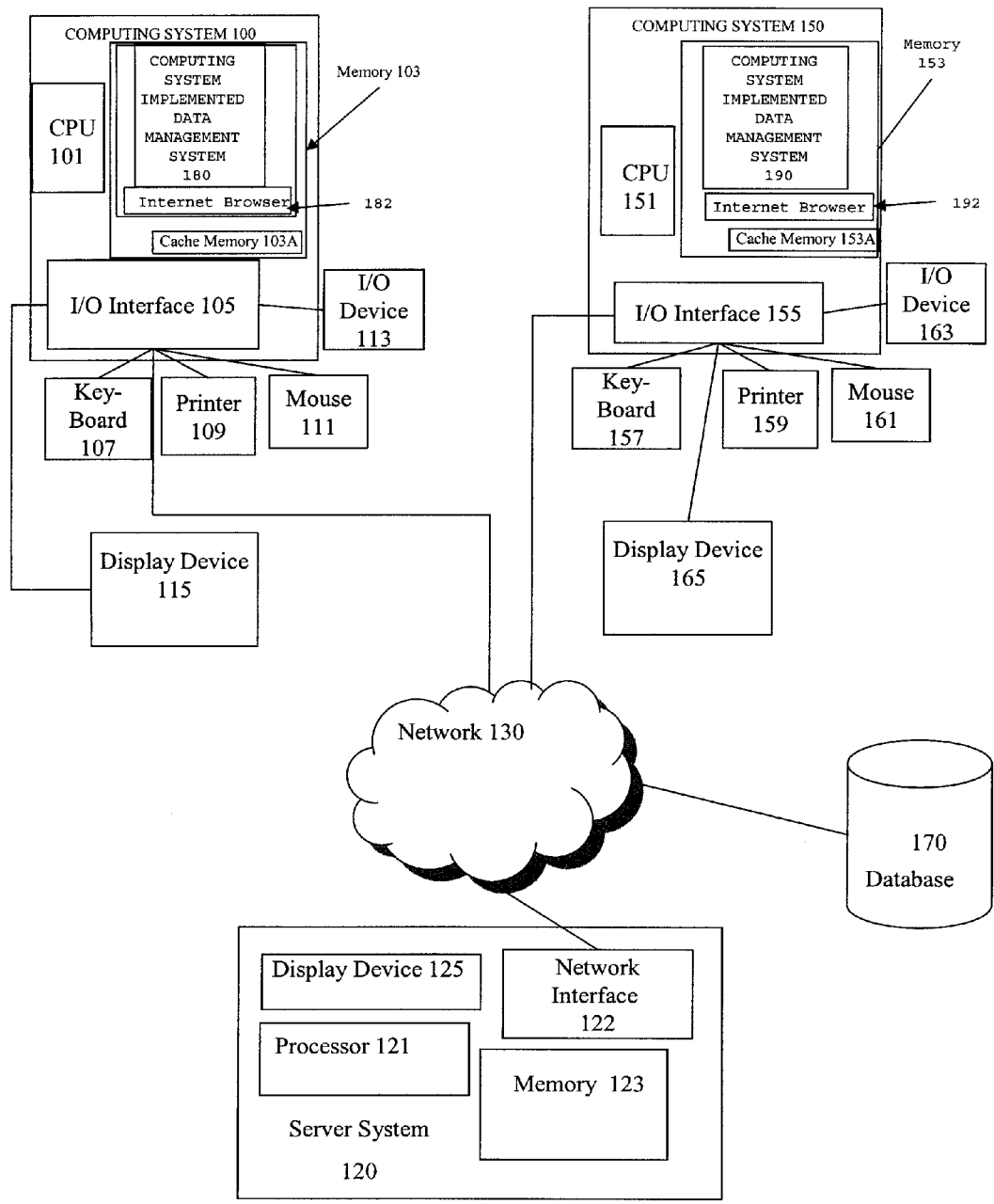
FIG. 1 is a block diagram of an exemplary hardware architecture for implementing one embodiment.

Common reference numerals are used throughout the FIG.s and the detailed description to indicate like elements. One skilled in the art will readily recognize that the above FIG.s are examples and that other architectures, modes of operation, orders of operation and elements/functions can be provided and implemented without departing from the characteristics and features of the invention, as set forth in the claims.

DETAILED DESCRIPTION

Embodiments will now be discussed with reference to the accompanying FIG. s, which depict one or more exemplary embodiments. Embodiments may be embodied in many different forms and should not be construed as limited to the embodiments set forth herein, shown in the FIG. s, and/or described below. Rather, these exemplary embodiments are provided to allow a complete disclosure that conveys the principles of the invention, as set forth in the claims, to those of skill in the art.

In accordance with one embodiment, a system and method for establishing a healthcare network across small businesses includes a process for establishing a healthcare network across small businesses whereby, in one embodiment, two or more small businesses and one or more healthcare insurance providers are enrolled in a small business employee healthcare network. In one embodiment, the one or more healthcare insurance providers then offer one or more healthcare insurance plans through the small business employee healthcare network at initial, or current minimum, bid prices. Employees of the enrolled small businesses are then provided an opportunity to view the one or more healthcare insurance plan offers. In one embodiment, interested employees of the enrolled small businesses then opt into one or more of the one or more healthcare insurance plan offers through the small business employee healthcare network. In one embodiment, as the number, and/or the profile, of the employees that opt into a given one of the one or more healthcare insurance plan offers increases and/or changes, and/or in response to bids from enrolled competitor healthcare insurance providers, the one or more healthcare insurance providers can change the bid prices for the one or more healthcare insurance plan offers. In one embodiment, after a specified time period, the healthcare insurance provider having offered the lowest bid is contracted to provide the one or more healthcare insurance plans, at the lowest bid price, to the employees that opted in.

In one embodiment, rather than providing individual employees of enrolled small businesses the ability to opt into the one or more healthcare insurance plans, the small businesses are grouped together and a specified percentage of each of the small businesses' employee base are committed by the small business employer to take part in any of the one or more healthcare insurance plans the group of small businesses opts into. In this way, the small business employer acts as an agent for the small business employees. This embodiment is particularly useful when the small business employer is paying a large part of, or all of, the healthcare insurance plan premiums for the employees.

FIG. 1 is a block diagram of an exemplary hardware architecture for implementing one embodiment of a system and method for establishing a healthcare network across small businesses, such as exemplary processes 200 (FIG. 2) and 300 (FIG. 3) discussed herein, that, returning to FIG. 1, includes: a computing system 100, e.g., a first computing system; a computing system 150, e.g., a second computing system; a server system 120; and a database 170, all operatively coupled by a network 130.

As seen in FIG. 1, computing system 100 typically includes a central processing unit (CPU) 101, an input/output (I/O) interface 105, and a memory system 103, including cache memory 103A. In one embodiment, memory system 103 includes all, or part, of a computing system implemented data management system 180, such as a computing system implemented payroll management system, or any computing system implemented data management system discussed herein, known in the art at the time of filing, and/or as developed thereafter.

Figure 2:
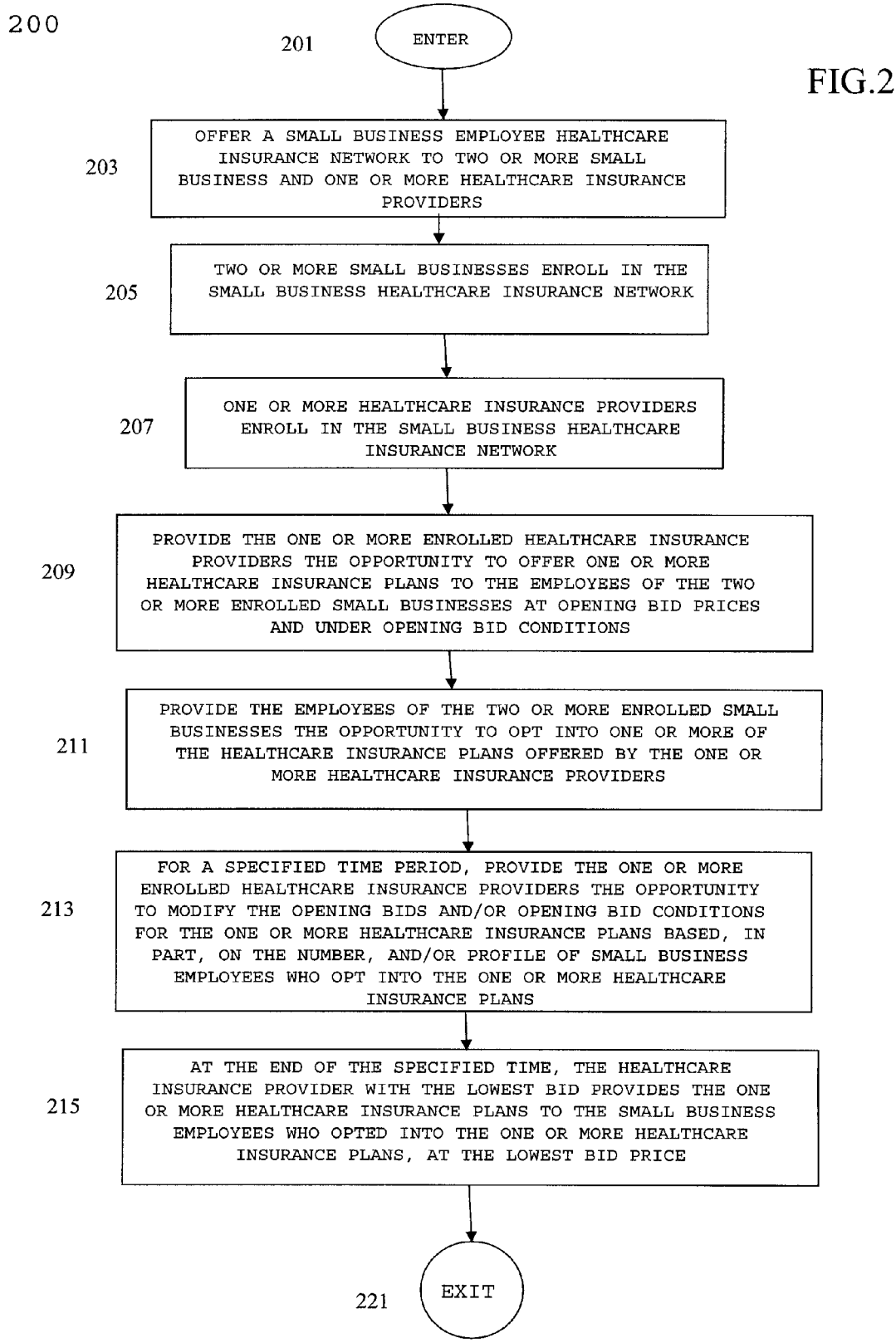
FIG. 2 is a flow chart depicting a process for establishing a healthcare network across small businesses in accordance with one embodiment.

In one embodiment, computing system implemented data management system 180 is stored, in whole, or in part, in memory system 103, and is used by, or includes, or is accessed by, a process for establishing a healthcare network across small businesses (not shown in FIG. 1, see FIG. 2).

Returning to FIG. 1, computing system 100 may further include standard user interface devices such as a keyboard 107, a mouse 111, a printer 109, and a display device 115, as well as, one or more standard input/output (I/O) devices 113, such as a compact disk (CD) or Digital Video Disc (DVD) drive, floppy disk drive, or other digital or waveform port, or other device capable of inputting data to, and outputting data from, computing system 100, whether available or known at the time of filing or as later developed. As discussed in more detail below, in one embodiment, data associated with a process for establishing a healthcare network across small businesses, and/or a computing system implemented data management system, and/or one or more healthcare insurance plans, and/or one or more employees profiles, and/or one or more small businesses, is transferred in whole, or in part, into computing system 100 via I/O device 113, such as from a CD, DVD, floppy disk, portable hard drive, memory stick, download site, or other medium and/or computer program product as discussed herein.

In one embodiment, computing system 100 also includes an Internet browser capability 182 that, in one embodiment, includes a search engine (not shown) and is stored, in whole, or in part in memory 103.

In one embodiment, data associated with a process for establishing a healthcare network across small businesses, and/or a computing system implemented data management system, and/or one or more healthcare insurance plans, and/or one or more employees profiles, and/or one or more small businesses, is stored, in whole, or in part, in memory system 103, and is used by, or is accessed by, a process for establishing a healthcare network across small businesses and/or one or more users. In one embodiment, computing system 100 is a computing system accessible by one or more users. In one embodiment, computing system 100 is used, and/or accessible, by another computing system, such as computing system 150 (discussed below).

Computing system 100 can be any computing system as discussed herein and/or as known in the art at the time of filing and/or as developed thereafter, that includes components that can execute all, or part, of a process for establishing a healthcare network across small businesses, and/or a computing system implemented data management system, in accordance with at least one of the embodiments as described herein.

Similarly, computing system 150 typically includes a CPU 150, an input/output (I/O) interface 155, and a memory system 153, including cache memory 153A. Similar to computing system 100, computing system 150 may further include standard user interface devices such as a keyboard 157, a mouse 161, a printer 159, and a display device 165, as well as, one or more standard input/output (I/O) devices 163, such as a compact disk (CD) or DVD drive, floppy disk drive, or other digital or waveform port, or other device capable of inputting data to, and outputting data from, computing system 150, whether available or known at the time of filing or as later developed.

In one embodiment, computing system 150 also includes an Internet browser capability 192 that, in one embodiment, includes a search engine (not shown) and is stored, in whole, or in part in memory 153.

In one embodiment, memory system 153 includes all, or part, of a computing system implemented data management system 190, such as any computing system implemented data management system discussed herein, known in the art at the time of filing, and/or as developed thereafter. In one embodiment, computing system implemented data management system 190 is stored, in whole, or in part, in memory system 153, and is used by, or includes, or is accessed by, a process for establishing a healthcare network across small businesses.

In one embodiment, data associated with a process for establishing a healthcare network across small businesses, and/or a computing system implemented data management system, and/or one or more healthcare insurance plans, and/or one or more employees profiles, and/or one or more small businesses, is stored, in whole, or in part, in memory system 153, and is used by, or is accessed by, a process for establishing a healthcare network across small businesses and/or one or more users.

In one embodiment, computing system 150 is a computing system accessible by one or more users. In one embodiment, computing system 150 is used, and/or accessible, by another computing system, such as computing system 100. Computing system 150 can be any computing system as discussed herein and/or as known in the art at the time of filing and/or as developed thereafter, that includes components that can execute all, or part, of a process for establishing a healthcare network across small businesses, and/or a computing system implemented data management system, in accordance with at least one of the embodiments as described herein.

As discussed in more detail below, in one embodiment, all, or part, of data associated with a process for establishing a healthcare network across small businesses, and/or a computing system implemented data management system, and/or one or more healthcare insurance plans, and/or one or more employees profiles, and/or one or more small businesses, can be loaded, in whole, or in part, into computing system 150 from computing system 100 for storage in memory system 153 and/or cache memory 153A.

Also shown in FIG. 1 is database 170. In one embodiment, database 170 is a data storage device, a designated server system or computing system, or a designated portion of one or more server systems or computing systems, such as computing systems 100, 150 and server system 120, or a distributed database, or an external and/or portable hard drive. In one embodiment, database 170 is a dedicated mass storage device implemented in software, hardware, or a combination of hardware and software. In one embodiment, database 170 includes a web-based function. As discussed in more detail below, in one embodiment, database 170 is under the control of, or otherwise accessible by, a process for establishing a healthcare network across small businesses, and/or a computing system implemented data management system.

In one embodiment, data associated with a process for establishing a healthcare network across small businesses, and/or a computing system implemented data management system, and/or one or more healthcare insurance plans, and/or one or more employees profiles, and/or one or more small businesses, is stored, in whole, or in part, in database 170, and is used by, or is accessed by, a process for establishing a healthcare network across small businesses. In one embodiment, database 170 is accessible by one or more users. In one embodiment, database 170 is used, and/or accessible, by a computing system, such as computing systems 100 and/or 150, and/or a server system, such as sever system 120 (discussed below).

In one embodiment, computing systems 100 and 150, and database 170, are coupled to a server system 120 through network 130. In one embodiment, server system 120 includes a server system display device 125, a server system processor 121, a server system memory 123, and a server system network interface 122.

In one embodiment, server system 120 is used in a station-to-station arrangement, such as a peer-to-peer, or hybrid peer-to peer, arrangement, as an indexing and/or central server used to connect a first computing system, such as computing system 100, and a second computing system, such as computing system 150.

In one embodiment, data associated with a process for establishing a healthcare network across small businesses, and/or a computing system implemented data management system, and/or one or more healthcare insurance plans, and/or one or more employees profiles, and/or one or more small businesses, is stored, in whole, or in part, in server system 120, and is used by, or is accessed by, a process for establishing a healthcare network across small businesses. In one embodiment, server system 120 is accessible by one or more users. In one embodiment, server system 120 is used, and/or accessible, by a computing system, such as computing systems 100 and/or 150, and/or one or more databases, such as database 170.

Network 130 can be any network or network system as discussed herein, and/or known in the art at the time of filing, and/or as developed after the time of filing, capable of allowing communication between two or more computing systems, server systems, and/or databases.

Those of skill in the art will readily recognize that the components shown in FIG. 1, such as computing systems 100 and 150, database 170, server system 120, and their respective components, are shown for illustrative purposes only and that architectures with more or fewer components can implement, and benefit from, one or more embodiments. Moreover, one or more components of computing system 100, computing system 150, database 170, and server system 120 may be located remotely from their respective system and accessed via network 130. In addition, the particular type of, and configuration of, computing systems 100 and 150, database 170, and server system 120 are not relevant.

As discussed in more detail below, in one embodiment, data associated with a process for establishing a healthcare network across small businesses, and/or a computing system implemented data management system, and/or one or more healthcare insurance plans, and/or one or more employees profiles, and/or one or more small businesses, is stored, in whole, or in part, in memory system 103 and/or cache memory 103A, of computing system 100, and/or memory system 153 and/or cache memory 153A of computing system 150, and/or in server memory system 123 of server system 120 and/or in database 170, and executed on computing system 100 and/or computing system 150. As used herein, a memory refers to a volatile memory, a non-volatile memory, or any combination of the two.

Although a process for establishing a healthcare network across small businesses, and/or a computing system implemented data management system are sometimes referred to herein, alternatively, as a process, an application, a module, a program, a component of a software system, a component of a software package, a component of a parent system, a plug-in, or a feature of a parent system, this terminology is illustrative only. In some embodiments, a process for establishing a healthcare network across small businesses, and/or a computing system implemented data management system, are capable of being called from an application or the operating system. In one embodiment, an application, process, or program is generally defined to be any executable code. Moreover, those of skill in the art will understand that when it is said that an application, process, or an operation takes some action, the action is the result of executing one or more instructions by a processor, such as CPUs 101 and 150, or server system processor 121. In one embodiment, execution of a process by CPU 101, CPU 150, or server system processor 121, results in the operations of an agent computer process (not shown) and/or a rule computer process (not shown).

In one embodiment, data associated with a process for establishing a healthcare network across small businesses, and/or a computing system implemented data management system, and/or one or more healthcare insurance plans, and/or one or more employees profiles, and/or one or more small businesses, are computer applications or processes and/or data implemented and/or run and/or stored, in full, or in part, in, or on, and/or through, a computer program product. Herein, a computer program product comprises a medium and/or I/O device configured to store or transport computer readable code, whether available or known at the time of filing or as later developed. Some examples of computer program products are CDs, DVDs, ROM cards, floppy discs, magnetic tapes, computer hard drives, portable hard drives, flash memory, volatile and non-volatile memory sticks, servers on a network, such as server system 120 of FIG. 1, and signals transmitted over a network, such as network 130 of FIG. 1, or other media or process capable of delivering computer readable data representing computer readable code, whether available or known at the time of filing or as later developed. This medium may belong to a computing system, such as computing systems 100 and 150 of FIG. 1, described above. However, in some embodiments, the medium also may be removable and/or remote from the computing system.

Process

Herein, the terms "healthcare service provider" and/or "healthcare services provider" include, but are not limited to, an individual person, persons, agencies, institutions, organizations, businesses, and/or other entities that provide medical treatment, medications, therapy, advice, and/or equipment. For example, herein, the term "healthcare service provider" includes, but is not limited to: doctors; nurses; technicians; therapists; pharmacists; laboratories; counselors; alternative medicine practitioners; medical facilities; doctor's offices; hospitals; emergency rooms; clinics; urgent care centers; alternative medicine clinics/facilities; physical therapy clinics/facilities; and any other entity providing general and/or specialized treatment, assessment, maintenance, therapy, medication, and/or advice relating to all, or any portion of, a healthcare service consumer's state of health, including but not limited to: general medical, specialized medical, surgical, dental, vision, psychological, and/or any other type of treatment, assessment, maintenance, therapy, medication, and/or advice.

Herein, the term "healthcare" includes, but is not limited to, any general and/or specialized treatment, assessment, maintenance, therapy, medication, and/or advice relating to all, or any portion of, a healthcare service consumer's state of health, including but not limited to: general medical, specialized medical, surgical, dental, vision, psychological, and/or any other type of treatment, assessment, maintenance, therapy, medication, and/or advice.

Herein, the term "medical treatment" includes, but is not limited to: one or more medications and/or medication regimes; physical therapy; recommended dietary changes; lab work, recommended activity level changes; other lifestyle changes; and/or surgical procedures; and/or any prescribed and/or suggested regime, medication, treatment, activity, avoided activity, and/or program designed to improve, maintain, and/or slow the degradation of, a healthcare consumer's state of health.

Herein, the terms "healthcare insurance plan", "healthcare benefit plan", and "health insurance program" are used interchangeably and include, but are not limited to, any policy, program, means and/or mechanism whereby a healthcare consumer is provided healthcare benefits and/or healthcare services, and/or entitlements to any from of healthcare.

Herein, the terms "healthcare insurance provider", "healthcare insurance service provider", "healthcare insurance plan provider" and "health services insurance provider" are used interchangeably and include, but are not limited to, any individual person, persons, agencies, institutions, organizations, businesses, and/or other entities that provide one or more healthcare insurance plans.

As used herein, the term "computing system", includes, but is not limited to: a desk-top computing system; a portable computer; a workstation; a two-way pager; a cellular telephone; a smart phone; a digital wireless telephone; a Personal Digital Assistant (PDA); a media player, i.e., an MP3 player and/or other music and/or video player; a server computer; an Internet appliance; or any other device that includes components that can execute all, or part, of any one of the processes and/or operations as described herein. In addition, as used herein, the term computing system, can denote, but is not limited to, computing systems made up of multiple: computers; wireless devices; cellular telephones; digital telephones; two-way pagers; PDAs; media players; server computers; or any desired combination of these devices, that are coupled to perform the processes and/or operations as described herein.

As used herein, the term "computing system implemented data management system" includes, but is not limited to: computing system implemented payroll management systems, packages, programs, modules, or applications; computing system implemented online banking systems, packages, programs, modules, or applications; computing system implemented social networking systems, packages, programs, modules, or applications; computing system implemented inventory systems, packages, programs, modules, or applications; computing system implemented personal and small business financial management systems, packages, programs, modules, or applications; computing system implemented business systems, packages, programs, modules, or applications; computing system implemented marketing device distribution systems, packages, programs, modules, or applications; computing system implemented financial institution financial management systems, packages, programs, modules, or applications; computing system implemented tax preparation systems, packages, programs, modules, or applications; computing system implemented accounting and/or invoicing systems, packages, programs, modules, or applications; computing system implemented business and/or point of sale systems, packages, programs, modules, or applications; computing system implemented healthcare management systems, packages, programs, modules, or applications and various other electronic data driven data management systems, packages, programs, modules, or applications, whether known at the time of filling or as developed later.

As used herein, the term "network" includes, but is not limited to, any network or network system such as, but not limited to, a peer-to-peer network, a hybrid peer-to-peer network, a Local Area Network (LAN), a Wide Area Network (WAN), a public network, such as the Internet, a private network, a cellular network, a combination of different network types, or other wireless, wired, and/or a wireless and wired combination network capable of allowing communication between two or more computing systems, whether available or known at the time of filing or as later developed.

As used herein, the term "database" includes, but is not limited to, any data storage mechanism known at the time of filing or as developed thereafter, such as, but not limited to: a data storage device; a designated server system or computing system, or a designated portion of one or more server systems or computing systems; a mobile computing system; a server system network; a distributed database; or an external and/or portable hard drive. Herein, the term "database" can refer to a dedicated mass storage device implemented in software, hardware, or a combination of hardware and software. Herein, the term "database" can refer to a web-based function. Herein, the term "database" can refer to any data storage means that is part of, or under the control of, any computing system, as discussed herein, known at the time of filing, or as developed thereafter.

In accordance with one embodiment, a system and method for establishing a healthcare network across small businesses includes a process for establishing a healthcare network across small businesses whereby, in one embodiment, two or more small businesses and one or more healthcare insurance providers are enrolled in a small business employee healthcare network. In one embodiment, the one or more healthcare insurance providers then offer one or more healthcare insurance plans through the small business employee healthcare network at initial, or current minimum, bid prices. Employees of the enrolled small businesses are then provided an opportunity to view the one or more healthcare insurance plan offers. In one embodiment, interested employees of the enrolled small businesses then opt into one or more of the one or more healthcare insurance plan offers through the small business employee healthcare network. In one embodiment, as the number, and/or the profile, of the employees that opt into a given one of the one or more healthcare insurance plan offers increases and/or changes, and/or in response to bids from enrolled competitor healthcare insurance providers, the one or more healthcare insurance providers can change the bid prices for the one or more healthcare insurance plan offers. In one embodiment, after a specified time period, the healthcare insurance provider having offered the lowest bid is contracted to provide the one or more healthcare insurance plans, at the lowest bid price, to the employees that opted in.

FIG. 2 is a flow chart depicting a process for establishing a healthcare network across small businesses 200 in accordance with one embodiment. Process for establishing a healthcare network across small businesses 200 begins at ENTER OPERATION 201 and process flow proceeds to OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203.

In one embodiment, at OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203 participation in a small business employee healthcare network is offered to two or more small businesses and one or more healthcare insurance providers.

In one embodiment, at OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203 participation in the small business employee healthcare network is offered to two or more small businesses, and has potential value to the two or more small businesses, based on the principle that through the small business employee healthcare network, and process for establishing a healthcare network across small businesses 200, the small business employers may have an opportunity to provide their employees access to healthcare insurance having desirable features at a cost that might not otherwise be available to them. This is because, through the small business employee healthcare network, and process for establishing a healthcare network across small businesses 200, the employees of multiple enrolled small businesses are grouped together to increase the number of plan participants.

Consequently, by their increased numbers, the risk to the healthcare insurance provider is spread over a greater premium base and the collective bargaining power of the employees of the multiple enrolled small businesses allows them to potentially be offered discounts that previously were only available to employees of large companies.

In one embodiment, at OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203 participation in the small business employee healthcare network is offered to at least one healthcare insurance provider, and has potential value to the at least one healthcare insurance provider, based on the principle that through the small business employee healthcare network, and process for establishing a healthcare network across small businesses 200, the at least one healthcare insurance provider may have an opportunity to provide healthcare insurance to more individuals at a lowered risk level than would otherwise be available. This is because, as noted above, through the small business employee healthcare network, and process for establishing a healthcare network across small businesses 200, the at least one healthcare insurance provider is given access to increased numbers of small business employees, and can insure them as a group to spread the risk to the healthcare insurance provider over a greater premium base. In addition, from the healthcare insurance provider's perspective, the actual number of employees of the multiple enrolled small businesses that opt into a given healthcare insurance plan is known in advance.

As a result, both the small business employers and the healthcare insurance providers are potentially benefited by participation in the small business employee healthcare network offered at OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203.

In one embodiment, at OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203 participation in the small business employee healthcare network is offered to the small business employers and/or the healthcare insurance providers directly, or through a computing system implemented data management system, such as computing system implemented payroll and/or data management systems 180 and/or 190 of FIG. 1, that implements, includes, is accessible by, and/or is otherwise associated with, process for establishing a healthcare network across small businesses 200 (FIG. 2).

Returning to FIG. 2, in one embodiment, at OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203 participation in the small business employee healthcare network is offered to the small business employers and/or the healthcare insurance providers by providing the small business employers and/or the healthcare insurance providers access to any database, such as database 170 of FIG. 1, any computing system, such as computing systems 100 and/or 150 of FIG. 1, and/or any server system, such as server system 120 of FIG. 1, or any web-site or other web-based system, associated with process for establishing a healthcare network across small businesses 200.

Returning to FIG. 2, in one embodiment, at OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203 participation in the small business employee healthcare network is offered to the small business employers and/or the healthcare insurance providers via the Internet.

Returning to FIG. 2, in one embodiment, at OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203 participation in the small business employee healthcare network is offered to the small business employers and/or the healthcare insurance providers through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1.

Returning to FIG. 2, in one embodiment, at OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203 participation in the small business employee healthcare network is offered to the small business employers and/or the healthcare insurance providers through e-mail or through text messaging.

In one embodiment, at OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203 participation in the small business employee healthcare network is offered to the small business employers and/or the healthcare insurance providers through traditional phone or postal service.

In one embodiment, at OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203 participation in the small business employee healthcare network is offered to the small business employers and/or the healthcare insurance providers using any method, apparatus, process or mechanism for offering, obtaining, and/or transferring data, images, screen displays, and/or text from one or more devices, computing systems, server systems, databases, web site/web functions and/or any systems to one or more other devices, computing systems, server systems, databases, web site/web functions and/or any systems, whether known at the time of filing or as thereafter developed.

In one embodiment, once participation in a small business employee healthcare network is offered to two or more small businesses and one or more healthcare insurance providers at OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203, process flow proceeds to TWO OR MORE SMALL BUSINESSES ENROLL IN THE SMALL BUSINESS HEALTHCARE INSURANCE NETWORK OPERATION 205.

In one embodiment, at TWO OR MORE SMALL BUSINESSES ENROLL IN THE SMALL BUSINESS HEALTHCARE INSURANCE NETWORK OPERATION 205, two or more small businesses enroll in the small business employee healthcare network and agree to abide by provided small business terms associated with the small business employee healthcare network.

In one embodiment, the small business terms associated with the small business employee healthcare network provided at TWO OR MORE SMALL BUSINESSES ENROLL IN THE SMALL BUSINESS HEALTHCARE INSURANCE NETWORK OPERATION 205 are contractual in nature and set forth the obligations, rights, payment terms, and default remedies associated with small businesses enrolled in the small business employee healthcare network.

In one embodiment, once two or more small businesses enroll in the small business employee healthcare network and agree to abide by provided small business terms associated with the small business employee healthcare network at TWO OR MORE SMALL BUSINESSES ENROLL IN THE SMALL BUSINESS HEALTHCARE INSURANCE NETWORK OPERATION 205, process flow proceeds to ONE OR MORE HEALTHCARE INSURANCE PROVIDERS ENROLL IN THE SMALL BUSINESS HEALTHCARE INSURANCE NETWORK OPERATION 207.

In one embodiment, at ONE OR MORE HEALTHCARE INSURANCE PROVIDERS ENROLL IN THE SMALL BUSINESS HEALTHCARE INSURANCE NETWORK OPERATION 207 one or more healthcare insurance providers enroll in the small business employee healthcare network and agree to abide by healthcare service provider terms associated with the small business employee healthcare network.

In one embodiment, the healthcare insurance provider terms associated with the small business employee healthcare network provided at ONE OR MORE HEALTHCARE INSURANCE PROVIDERS ENROLL IN THE SMALL BUSINESS HEALTHCARE INSURANCE NETWORK OPERATION 207 are contractual in nature and set forth the obligations, rights, payment terms, and default remedies associated with healthcare insurance providers enrolled in the small business employee healthcare network.

In one embodiment, once one or more healthcare insurance providers enroll in the small business employee healthcare network and agree to abide by healthcare service provider terms associated with the small business employee healthcare network at ONE OR MORE HEALTHCARE INSURANCE PROVIDERS ENROLL IN THE SMALL BUSINESS HEALTHCARE INSURANCE NETWORK OPERATION 207, process flow proceeds to PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209.

In one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers of ONE OR MORE HEALTHCARE INSURANCE PROVIDERS ENROLL IN THE SMALL BUSINESS HEALTHCARE INSURANCE NETWORK OPERATION 207 are provided the opportunity and capability to offer one or more healthcare insurance plans to the employees of the two or more enrolled small businesses of TWO OR MORE SMALL BUSINESSES ENROLL IN THE SMALL BUSINESS HEALTHCARE INSURANCE NETWORK OPERATION 205 through the small business employee healthcare insurance network of OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203.

In one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers are provided the opportunity and capability to offer one or more healthcare insurance plans to the employees of the two or more enrolled small businesses through an employee portal, such as an employee website maintained by the process for establishing a healthcare network across small businesses.

In one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers are provided the opportunity and capability to offer one or more healthcare insurance plans to the employees of the two or more enrolled small businesses through an employee portal, such as an employee website and/or database maintained by the small business employer. In one embodiment, the employee website is the same website used by employees to track their pay records, accumulated vacation time, sick days, and other payroll related data.

In one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers are provided the opportunity and capability to offer one or more healthcare insurance plans to the employees of the two or more enrolled small businesses through an attachment to the employees paycheck and/or direct deposit notifications.

In one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers are provided the opportunity and capability to offer one or more healthcare insurance plans to the employees of the two or more enrolled small businesses on a periodic basis, such as an annual, semi annual basis, quarterly basis, and/or monthly basis.

In one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers are provided the opportunity and capability to offer one or more healthcare insurance plans to the employees of the two or more enrolled small businesses through a computing system implemented data management system, such as 180 and/or 190 of FIG. 1, and/or computing system implemented payroll management system, that implements, includes, is accessible by, and/or is otherwise associated with, process for establishing a healthcare network across small businesses 200 (FIG. 2).

Returning to FIG. 2, in one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers are provided the opportunity and capability to offer one or more healthcare insurance plans to the employees of the two or more enrolled small businesses by providing the employees access to any database, such as database 170 of FIG. 1, any computing system, such as computing systems 100 and/or 150 of FIG. 1, and/or any server system, such as server system 120 of FIG. 1, or any web-site or other web-based system, associated with process for establishing a healthcare network across small businesses 200 (FIG. 2).

In one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers are provided the opportunity and capability to offer one or more healthcare insurance plans to the employees of the two or more enrolled small businesses via the Internet.

In one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers are provided the opportunity and capability to offer one or more healthcare insurance plans to the employees of the two or more enrolled small businesses through any network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1.

Returning to FIG. 2, in one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers are provided the opportunity and capability to offer one or more healthcare insurance plans to the employees of the two or more enrolled small businesses through e-mail or through text messaging.

Returning to FIG. 2, in one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers are provided the opportunity and capability to offer one or more healthcare insurance plans to the employees of the two or more enrolled small businesses through traditional postal and/or telephone service.

In one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers are provided the opportunity and capability to offer one or more healthcare insurance plans to the employees of the two or more enrolled small businesses using any method, apparatus, process or mechanism for offering, obtaining, and/or transferring data, images, screen displays, and/or text from one or more devices, computing systems, server systems, databases, web site/web functions and/or any systems to one or more other devices, computing systems, server systems, databases, web site/web functions and/or any systems, whether known at the time of filing or as thereafter developed.

In one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers are provided the opportunity and capability to offer one or more healthcare insurance plans to the employees of the two or more enrolled small businesses at an opening, or initial, bid price, or premium. As discussed below, in one embodiment, the initial bid price of PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 can be changed by the one or more enrolled healthcare insurance providers as data is collected regarding the number, and/or type of employees, opting into a given healthcare insurance plan.

In one embodiment, at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 the one or more enrolled healthcare insurance providers are provided the opportunity and capability to offer one or more healthcare insurance plans to the employees of the two or more enrolled small businesses under opening, or initial, bid conditions such as, but not limited to, specified: deductible amounts; percentages of medical costs covered; in-network healthcare providers; percentages of medical costs covered for in-network healthcare providers; percentages of medical costs covered for out-of-network healthcare providers; medical treatments covered; yearly coverage cost caps; co-payments; and/or any other coverage conditions or limits desired.

As discussed below, in one embodiment, the initial bid conditions of PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 can be changed by the one or more enrolled healthcare insurance providers as data is collected regarding the number, and/or type of employees, opting into a given healthcare insurance plan.

In one embodiment, once the one or more enrolled healthcare insurance providers of ONE OR MORE HEALTHCARE INSURANCE PROVIDERS ENROLL IN THE SMALL BUSINESS HEALTHCARE INSURANCE NETWORK OPERATION 207 are provided the opportunity and capability to offer one or more healthcare insurance plans to the employees of the two or more enrolled small businesses of TWO OR MORE SMALL BUSINESSES ENROLL IN THE SMALL BUSINESS HEALTHCARE INSURANCE NETWORK OPERATION 205, through the small business employee healthcare insurance network of OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203 at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209, process flow proceeds to PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211.

In one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211 employees of the two or more enrolled small businesses of TWO OR MORE SMALL BUSINESSES ENROLL IN THE SMALL BUSINESS HEALTHCARE INSURANCE NETWORK OPERATION 205 can view the conditions and/or price of one or more of the one or more healthcare insurance plans of PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 offered by the one or more enrolled healthcare insurance providers of ONE OR MORE HEALTHCARE INSURANCE PROVIDERS ENROLL IN THE SMALL BUSINESS HEALTHCARE INSURANCE NETWORK OPERATION 207.

In one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211 employees of the two or more enrolled small businesses of TWO OR MORE SMALL BUSINESSES ENROLL IN THE SMALL BUSINESS HEALTHCARE INSURANCE NETWORK OPERATION 205 choose to participate in, i.e., opt in, to one or more of the one or more healthcare insurance plans of PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 offered by the one or more enrolled healthcare insurance providers of ONE OR MORE HEALTHCARE INSURANCE PROVIDERS ENROLL IN THE SMALL BUSINESS HEALTHCARE INSURANCE NETWORK OPERATION 207.

In one embodiment, once an employee of the two or more enrolled small businesses opts into one or more of the one or more healthcare insurance plans offered by the one or more enrolled healthcare insurance providers at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211, the employee, and/or small business employer, is committed to accept the one or more healthcare insurance plans offered by the one or more enrolled healthcare insurance providers they opt into as long as the price of the one or more healthcare insurance plans remains at the opt in price, or lower.

In other embodiments, once an employee of the two or more enrolled small businesses opts into one or more of the one or more healthcare insurance plans offered by the one or more enrolled healthcare insurance providers at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211, the employee, and/or small business employer, is committed to accept one or more healthcare insurance plans offered by the one or more enrolled healthcare insurance providers they opt into as long as the final price of the one or more healthcare insurance plans is in a specified range.

In other embodiments, once an employee of the two or more enrolled small businesses opts into one or more of the one or more healthcare insurance plans offered by the one or more enrolled healthcare insurance providers at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211, the employee, and/or small business employer, is committed to accept the one or more healthcare insurance plans offered by the one or more enrolled healthcare insurance providers the employee opted into according to the terms provided, and agreed to, at TWO OR MORE SMALL BUSINESSES ENROLL IN THE SMALL BUSINESS HEALTHCARE INSURANCE NETWORK OPERATION 205.

In one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211 employees of the two or more enrolled small businesses can opt in to one or more of the one or more healthcare insurance plans of PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 offered by the one or more enrolled healthcare insurance providers of ONE OR MORE HEALTHCARE INSURANCE PROVIDERS ENROLL IN THE SMALL BUSI- NESS HEALTHCARE INSURANCE NETWORK OPERATION 207 for a specified time period and/or during specified dates.

In one embodiment, the specified time period an employee of the two or more enrolled small businesses can opt into one or more of the one or more healthcare insurance plans offered by the one or more enrolled healthcare insurance providers is an open enrollment period established by the healthcare insurance providers of ONE OR MORE HEALTHCARE INSURANCE PROVIDERS ENROLL IN THE SMALL BUSINESS HEALTHCARE INSURANCE NETWORK OPERATION 207, and/or the small business employers of TWO OR MORE SMALL BUSINESSES ENROLL IN THE SMALL BUSINESS HEALTHCARE INSURANCE NETWORK OPERATION 205, and/or process for establishing a healthcare network across small businesses 200.

In one embodiment, the open enrollment period is set based on the estimated period of time required to attain a threshold number of new potential employees to opt into the one or more healthcare insurance plans at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211.

In one embodiment, the open enrollment period is variable and varies according to when a threshold number of new employees opt into the one or more healthcare insurance plans at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211.

In one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211 the employees of two or more enrolled small businesses can view the conditions of, and/or opt into, one or more of the one or more healthcare insurance plans offered by the one or more enrolled healthcare insurance providers through an employee portal, such as an employee website maintained by the process for establishing a healthcare network across small businesses.

In one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211 the employees of two or more enrolled small businesses can view the conditions of, and/or opt into, one or more of the one or more healthcare insurance plans offered by the one or more enrolled healthcare insurance providers through an employee portal, such as an employee website and/or database maintained by the small business employer. In one embodiment, the employee website is the same website used by employees to track their pay records, accumulated vacation time, sick days, and other payroll related data.

In one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211 the employees of two or more enrolled small businesses can view the conditions of, and/or opt into, one or more of the one or more healthcare insurance plans offered by the one or more enrolled healthcare insurance providers as part of new employee packages, or as part of new employee processing.

In one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211 the employees of two or more enrolled small businesses can view the conditions of, and/or opt into, one or more of the one or more healthcare insurance plans offered by the one or more enrolled healthcare insurance providers through a computing system implemented data management system, such as 180 and/or 190 of FIG. 1, and/or computing system implemented payroll management system, that implements, includes, is accessible by, and/or is otherwise associated with, process for establishing a healthcare network across small businesses 200 (FIG. 2).

Returning to FIG. 2, in one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211 the employees of two or more enrolled small businesses can view the conditions of, and/or opt into, one or more of the one or more healthcare insurance plans offered by the one or more enrolled healthcare insurance providers by providing the employees access to any database, such as database 170 of FIG. 1, any computing system, such as computing systems 100 and/or 150 of FIG. 1, and/or any server system, such as server system 120 of FIG. 1, or any web-site or other web-based system, associated with process for establishing a healthcare network across small businesses 200 (FIG. 2).

In one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211 the employees of two or more enrolled small businesses can view the conditions of, and/or opt into, one or more of the one or more healthcare insurance plans offered by the one or more enrolled healthcare insurance providers via the Internet.

In one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211 the employees of two or more enrolled small businesses can view the conditions of, and/or opt into, one or more of the one or more healthcare insurance plans offered by the one or more enrolled healthcare insurance providers through any network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1.

Returning to FIG. 2, in one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSUR- ANCE PLANS OFFERED BY THE ONE OR MORE HEALTHCARE INSURANCE PROVIDERS OPERATION 211 the employees of two or more enrolled small businesses can view the conditions of, and/or opt into, one or more of the one or more healthcare insurance plans offered by the one or more enrolled healthcare insurance providers through e-mail or through text messaging.

Returning to FIG. 2, in one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211 the employees of two or more enrolled small businesses can view the conditions of, and/or opt into, one or more of the one or more healthcare insurance plans offered by the one or more enrolled healthcare insurance providers through traditional postal and/or telephone service.

In one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211 the employees of two or more enrolled small businesses can view the conditions of, and/or opt into, one or more of the one or more healthcare insurance plans offered by the one or more enrolled healthcare insurance providers by filling out a printed form and submitting the filled out printed form to a designated party.

In one embodiment, at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211 the employees of two or more enrolled small businesses can view the conditions of, and/or opt into, one or more of the one or more healthcare insurance plans offered by the one or more enrolled healthcare insurance providers using any method, apparatus, process or mechanism for offering, obtaining, and/or transferring data, images, screen displays, and/or text from one or more devices, computing systems, server systems, databases, web site/web functions and/or any systems to one or more other devices, computing systems, server systems, databases, web site/web functions and/or any systems, whether known at the time of filing or as thereafter developed.

In one embodiment, once employees of the two or more enrolled small businesses of TWO OR MORE SMALL BUSINESSES ENROLL IN THE SMALL BUSINESS HEALTHCARE INSURANCE NETWORK OPERATION 205 are provided the ability to view the conditions and/or price, and/or opt into, one or more of the one or more healthcare insurance plans of PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 offered by the one or more enrolled healthcare insurance providers of ONE OR MORE HEALTHCARE INSURANCE PROVIDERS ENROLL IN THE SMALL BUSINESS HEALTHCARE INSURANCE NETWORK OPERATION 207 at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211, process flow proceeds to FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS EMPLOYEES WHO OPT INTO THE ONE OR MORE HEALTHCARE INSURANCE PLANS OPERATION 213.

In one embodiment, at FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS EMPLOYEES WHO OPT INTO THE ONE OR MORE HEALTHCARE INSURANCE PLANS OPERATION 213 during the specified time period of PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211, the one or more enrolled healthcare insurance providers of ONE OR MORE HEALTHCARE INSURANCE PROVIDERS ENROLL IN THE SMALL BUSINESS HEALTHCARE INSURANCE NETWORK OPERATION 207 can change the bid price, and/or one or more bid conditions, associated with any one of the one or more healthcare insurance plans offered at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209.

In one embodiment, at FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS EMPLOYEES WHO OPT INTO THE ONE OR MORE HEALTHCARE INSURANCE PLANS OPERATION 213 the one or more enrolled healthcare insurance providers change the bid price for the one or more healthcare insurance plans offered, and/or the bid conditions, based, at least in part, on the number of employees of the two or more enrolled small businesses that opt into the one or more healthcare insurance plans at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211. In this way, the one or more enrolled healthcare insurance providers change the bid price for the one or more healthcare insurance plans offered as the number of employees that opt in increases, thereby spreading the risk factor over a greater premium base and reducing the healthcare insurance providers' exposure.

In one embodiment, at FOR A SPECIFIED TIME PERIOD, PROVIDE THE ONE OR MORE ENROLLED HEALTHCARE INSURANCE PROVIDERS THE OPPOR- TUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS EMPLOYEES WHO OPT INTO THE ONE OR MORE HEALTHCARE INSURANCE PLANS OPERATION 213 the one or more enrolled healthcare insurance providers change the bid price for the one or more healthcare insurance plans offered and/or the bid conditions, based, at least in part, on the profiles of the employees of the two or more enrolled small businesses that opt into the one or more healthcare insurance plans at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211. In this way, the one or more enrolled healthcare insurance providers change the bid price for the one or more healthcare insurance plans offered as the profile data, such as average age of employees that opt in, changes, thereby changing the risk the healthcare insurance providers' exposure.

In one embodiment, at FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS EMPLOYEES WHO OPT INTO THE ONE OR MORE HEALTHCARE INSURANCE PLANS OPERATION 213, the one or more enrolled healthcare insurance providers of ONE OR MORE HEALTHCARE INSURANCE PROVIDERS ENROLL IN THE SMALL BUSINESS HEALTHCARE INSURANCE NETWORK OPERATION 207 competitively bid against each other. Consequently, in one embodiment, at FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS EMPLOYEES WHO OPT INTO THE ONE OR MORE HEALTHCARE INSURANCE PLANS OPERATION 213 the one or more enrolled healthcare insurance providers change the bid price for the one or more healthcare insurance plans offered, and/or the bid conditions, based, at least in part, on a competitive response to bid prices and/or the bid conditions offered by other enrolled healthcare insurance providers.

In one embodiment, at FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS EMPLOYEES WHO OPT INTO THE ONE OR MORE HEALTHCARE INSURANCE PLANS OPERATION 213 the one or more enrolled healthcare insurance providers change the bid price for the one or more healthcare insurance plans offered, and/or the bid conditions, based, at least in part, any combination of the factors discussed above, and/or for any other reason.

In one embodiment, once the one or more enrolled healthcare insurance providers of ONE OR MORE HEALTHCARE INSURANCE PROVIDERS ENROLL IN THE SMALL BUSINESS HEALTHCARE INSURANCE NETWORK OPERATION 207 are given the opportunity to change the bid price, and/or one or more bid conditions, associated with any one of the one or more healthcare insurance plans offered at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209, during the specified time period of PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211, at FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS EMPLOYEES WHO OPT INTO THE ONE OR MORE HEALTHCARE INSURANCE PLANS OPERATION 213, process flow proceeds to AT THE END OF THE SPECIFIED TIME, THE HEALTHCARE INSURANCE PROVIDER WITH THE LOWEST BID PROVIDES THE ONE OR MORE HEALTHCARE INSURANCE PLANS TO THE SMALL BUSINESS EMPLOYEES WHO OPTED INTO THE ONE OR MORE HEALTHCARE INSURANCE PLANS, AT THE LOWEST BID PRICE OPERATION 215.

In one embodiment, at AT THE END OF THE SPECIFIED TIME, THE HEALTHCARE INSURANCE PROVIDER WITH THE LOWEST BID PROVIDES THE ONE OR MORE HEALTHCARE INSURANCE PLANS TO THE SMALL BUSINESS EMPLOYEES WHO OPTED INTO THE ONE OR MORE HEALTHCARE INSURANCE PLANS, AT THE LOWEST BID PRICE OPERATION 215 at the end of the specified time period, the healthcare insurance provider having offered the lowest bid, and/or most favorable bid conditions, is contracted to provide the one or more healthcare insurance plans to the employees of the two or more enrolled small businesses that opted into the one or more healthcare insurance plans at the lowest bid price, and under the stated bid conditions.

In one embodiment, at AT THE END OF THE SPECIFIED TIME, THE HEALTHCARE INSURANCE PROVIDER WITH THE LOWEST BID PROVIDES THE ONE OR MORE HEALTHCARE INSURANCE PLANS TO THE SMALL BUSINESS EMPLOYEES WHO OPTED INTO THE ONE OR MORE HEALTHCARE INSURANCE PLANS, AT THE LOWEST BID PRICE OPERATION 215 at the end of the specified time period of PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211, the healthcare insurance provider of ONE OR MORE HEALTHCARE INSURANCE PROVIDERS ENROLL IN THE SMALL BUSINESS HEALTHCARE INSURANCE NETWORK OPERATION 207 having offered the lowest bid, and/or most favorable bid conditions, at FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS EMPLOYEES WHO OPT INTO THE ONE OR MORE HEALTHCARE INSURANCE PLANS OPERATION 213 is contractually obligated to provide the one or more healthcare insurance plans of PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 to the employees of the two or more enrolled small businesses of TWO OR MORE SMALL BUSINESSES ENROLL IN THE SMALL BUSINESS HEALTHCARE INSURANCE NETWORK OPERATION 205 that opted into the one or more healthcare insurance plans at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211, at the lowest bid price, and under the stated bid conditions of FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS EMPLOYEES WHO OPT INTO THE ONE OR MORE HEALTHCARE INSURANCE PLANS OPERATION 213.

In one embodiment, under the terms provided, and agreed to, at TWO OR MORE SMALL BUSINESSES ENROLL IN THE SMALL BUSINESS HEALTHCARE INSURANCE NETWORK OPERATION 205 and/or ONE OR MORE HEALTHCARE INSURANCE PROVIDERS ENROLL IN THE SMALL BUSINESS HEALTHCARE INSURANCE NETWORK OPERATION 207, the two or more enrolled small businesses of TWO OR MORE SMALL BUSINESSES ENROLL IN THE SMALL BUSINESS HEALTHCARE INSURANCE NETWORK OPERATION 205 keep records of what employees are enrolled in which one of the one or more healthcare insurance plans offered at PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209 and accepted/opted into at PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211. In one embodiment, the two or more enrolled small businesses use the records to deduct the proper amounts from a given employees pay to cover the employee's share of the one or more healthcare insurance plans opted into by the employee. In one embodiment, the deducted amounts, along with the small business employer's contribution, are aggregated for all the small business's employees having opted into the one or more healthcare insurance plans and premium payments are made as a lump sum to the healthcare insurance provider each pay period, or as contracted/stipulated in the small business employee healthcare network terms. In one embodiment, the records and payments are collected, kept, and/or made using one or more computing system implemented data management systems.

In one embodiment, once at the end of the specified time period, the healthcare insurance provider having offered the lowest bid, and/or most favorable bid conditions, is contracted to provide the one or more healthcare insurance plans to the employees of the two or more enrolled small businesses that opted into the one or more healthcare insurance plans at the lowest bid price, and under the stated bid conditions at AT THE END OF THE SPECIFIED TIME, THE HEALTHCARE INSURANCE PROVIDER WITH THE LOWEST BID PROVIDES THE ONE OR MORE HEALTHCARE INSURANCE PLANS TO THE SMALL BUSINESS EMPLOYEES WHO OPTED INTO THE ONE OR MORE HEALTHCARE INSURANCE PLANS, AT THE LOWEST BID PRICE OPERATION 215 process flow proceeds to EXIT OPERATION 221.

In one embodiment, at EXIT OPERATION 221 process for establishing a healthcare network across small businesses 200 is exited to await new data.

In the discussion above, certain aspects of one embodiment include process steps and/or operations and/or instructions described herein for illustrative purposes in a particular order and/or grouping. However, the particular order and/or grouping shown and discussed herein are illustrative only and not limiting. Those of skill in the art will recognize that other orders and/or grouping of the process steps and/or operations and/or instructions are possible and, in some embodiments, one or more of the process steps and/or operations and/or instructions discussed above can be combined and/or deleted. In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein do not limit the scope of the invention as claimed below.

In one embodiment, rather than providing individual employees of enrolled small businesses the ability to opt into the one or more healthcare insurance plans, the small businesses are grouped together and a specified percentage of each of the small businesses' employee base are committed by the small business employer to take part in any of the one or more healthcare insurance plans the group of small businesses opts into. In this way, the small business employer acts as an agent for the small business employees. This embodiment is particularly useful when the small business employer is paying a large part of, or all of, the healthcare insurance plan premiums for the employees.

Figure 3:
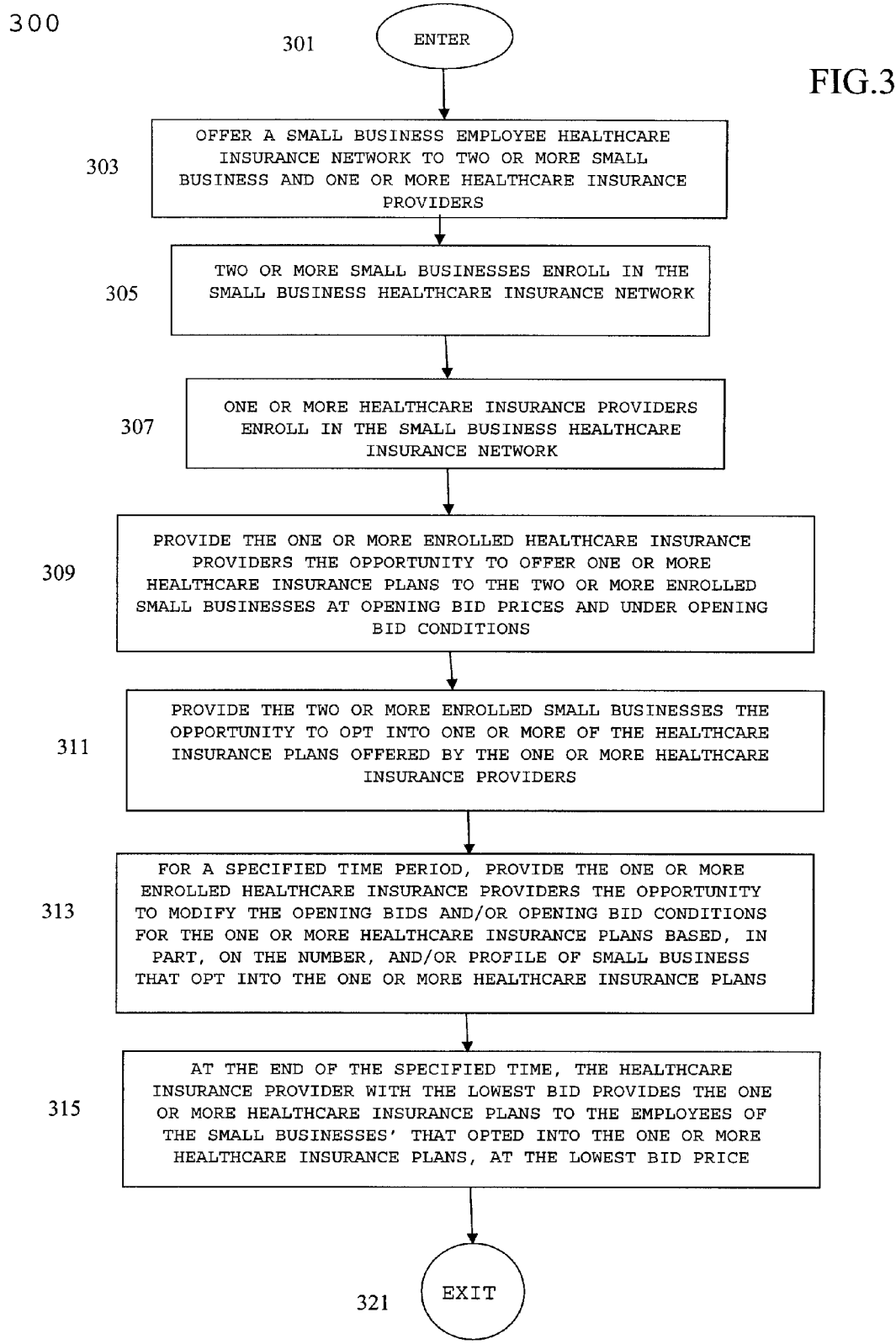
FIG. 3 is a flow chart depicting a process for establishing a healthcare network across small businesses in accordance with one embodiment.

FIG. 3 is a flow chart depicting a process for establishing a healthcare network across small businesses 300 in accordance with one embodiment. Process for establishing a healthcare network across small businesses 300 begins at ENTER OPERATION 301 and process flow proceeds to OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 303.

In one embodiment, OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 303; TWO OR MORE SMALL BUSINESSES ENROLL IN THE SMALL BUSINESS HEALTH- CARE INSURANCE NETWORK OPERATION 305; ONE OR MORE HEALTHCARE INSURANCE PROVIDERS ENROLL IN THE SMALL BUSINESS HEALTHCARE INSURANCE NETWORK OPERATION 307; PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE TWO OR MORE ENROLLED SMALL BUSINESSES AT OPENING BID PRICES AND UNDER OPENING BID CONDITIONS OPERATION 309; PROVIDE THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 311; FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS THAT OPT INTO THE ONE OR MORE HEALTHCARE INSURANCE PLANS OPERATION 313; and AT THE END OF THE SPECIFIED TIME, THE HEALTHCARE INSURANCE PROVIDER WITH THE LOWEST BID PROVIDES THE ONE OR MORE HEALTHCARE INSURANCE PLANS TO THE EMPLOYEES OF THE SMALL BUSINESSES' THAT OPTED INTO THE ONE OR MORE HEALTHCARE INSURANCE PLANS, AT THE LOWEST BID PRICE OPERATION 315 of process for establishing a healthcare network across small businesses 300 of FIG. 3 are substantially similar to OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203; TWO OR MORE SMALL BUSINESSES ENROLL IN THE SMALL BUSINESS HEALTHCARE INSURANCE NETWORK OPERATION 205; ONE OR MORE HEALTHCARE INSURANCE PROVIDERS ENROLL IN THE SMALL BUSINESS HEALTHCARE INSURANCE NETWORK OPERATION 207; PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE EMPLOYEES OF THE TWO OR MORE ENROLLED SMALL BUSINESSES AT OPENING BID PRICES AND UNDER OPENING BID CONDITIONS OPERATION 209; PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211; FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS EMPLOYEES WHO OPT INTO THE ONE OR MORE HEALTHCARE INSURANCE PLANS OPERATION 213; and AT THE END OF THE SPECIFIED TIME, THE HEALTHCARE INSURANCE PROVIDER WITH THE LOWEST BID PROVIDES THE ONE OR MORE HEALTHCARE INSURANCE PLANS TO THE SMALL BUSINESS EMPLOYEES WHO OPTED INTO THE ONE OR MORE HEALTHCARE INSURANCE PLANS, AT THE LOWEST BID PRICE OPERATION 215 of process for establishing a healthcare network across small businesses 200 of FIG. 2.

As noted, the only difference is that, using process for establishing a healthcare network across small businesses 300, rather than providing individual employees of enrolled small businesses the ability to opt into the one or more healthcare insurance plans, as is done according process for establishing a healthcare network across small businesses 200, the small businesses are grouped together and a specified minimum percentage of each of the small businesses' employee base are committed by the small business employer to take part in any of the one or more healthcare insurance plans the group of small businesses opts into.

Consequently, the discussion above with respect to OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 203; TWO OR MORE SMALL BUSINESSES ENROLL IN THE SMALL BUSINESS HEALTHCARE INSURANCE NETWORK OPERATION 205; ONE OR MORE HEALTHCARE INSURANCE PROVIDERS ENROLL IN THE SMALL BUSINESS HEALTHCARE INSURANCE NETWORK OPERATION 207; PROVIDE THE EMPLOYEES OF THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 211; FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS EMPLOYEES WHO OPT INTO THE ONE OR MORE HEALTHCARE INSURANCE PLANS OPERATION 213; and AT THE END OF THE SPECIFIED TIME, THE HEALTHCARE INSURANCE PROVIDER WITH THE LOWEST BID PROVIDES THE ONE OR MORE HEALTHCARE INSURANCE PLANS TO THE SMALL BUSINESS EMPLOYEES WHO OPTED INTO THE ONE OR MORE HEALTHCARE INSURANCE PLANS, AT THE LOWEST BID PRICE OPERATION 215 of process for establishing a healthcare network across small businesses 200 of FIG. 2 is applicable to, and incorporated here for OFFER A SMALL BUSINESS EMPLOYEE HEALTHCARE INSURANCE NETWORK TO TWO OR MORE SMALL BUSINESS AND ONE OR MORE HEALTHCARE INSURANCE PROVIDERS OPERATION 303; TWO OR MORE SMALL BUSINESSES ENROLL IN THE SMALL BUSINESS HEALTHCARE INSURANCE NETWORK OPERATION 305; ONE OR MORE HEALTHCARE INSURANCE PROVIDERS ENROLL IN THE SMALL BUSINESS HEALTHCARE INSURANCE NETWORK OPERATION 307; PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE TWO OR MORE ENROLLED SMALL BUSINESSES AT OPENING BID PRICES AND UNDER OPENING BID CONDITIONS OPERATION 309; PROVIDE THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 311; FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS THAT OPT INTO THE ONE OR MORE HEALTHCARE INSURANCE PLANS OPERATION 313; and AT THE END OF THE SPECIFIED TIME, THE HEALTHCARE INSURANCE PROVIDER WITH THE LOWEST BID PROVIDES THE ONE OR MORE HEALTHCARE INSURANCE PLANS TO THE EMPLOYEES OF THE SMALL BUSINESSES' THAT OPTED INTO THE ONE OR MORE HEALTHCARE INSURANCE PLANS, AT THE LOWEST BID PRICE OPERATION 315 of process for establishing a healthcare network across small businesses 300 of FIG. 3.

In one embodiment, once at the end of the specified time period of PROVIDE THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 311, the healthcare insurance provider of ONE OR MORE HEALTHCARE INSURANCE PROVIDERS ENROLL IN THE SMALL BUSINESS HEALTHCARE INSURANCE NETWORK OPERATION 307 having offered the lowest bid, and/or most favorable bid conditions, at FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS THAT OPT INTO THE ONE OR MORE HEALTHCARE INSURANCE PLANS OPERATION 313 is contractually obligated to provide the one or more healthcare insurance plans of PROVIDE THE ONE OR MORE ENROLLED HEALTHCARE INSURANCE PROVIDERS THE OPPORTUNITY TO OFFER ONE OR MORE HEALTHCARE INSURANCE PLANS TO THE TWO OR MORE ENROLLED SMALL BUSINESSES AT OPENING BID PRICES AND UNDER OPENING BID CONDITIONS OPERATION 309 to the employees of the two or more enrolled small businesses of TWO OR MORE SMALL BUSINESSES ENROLL IN THE SMALL BUSINESS HEALTHCARE INSURANCE NETWORK OPERATION 305 that opted into the one or more healthcare insurance plans at PROVIDE THE TWO OR MORE ENROLLED SMALL BUSINESSES THE OPPORTUNITY TO OPT INTO ONE OR MORE OF THE HEALTHCARE INSURANCE PLANS OFFERED BY THE ONE OR MORE HEALTHCARE INSURANCE PROVIDERS OPERATION 311, at the lowest bid price, and under the stated bid conditions of FOR A SPECIFIED TIME PERIOD, PROVIDE THE ONE OR MORE ENROLLED HEALTHCARE INSURANCE PROVIDERS THE OPPORTUNITY TO MODIFY THE OPENING BIDS AND/OR OPENING BID CONDITIONS FOR THE ONE OR MORE HEALTHCARE INSURANCE PLANS BASED, IN PART, ON THE NUMBER, AND/OR PROFILE OF SMALL BUSINESS THAT OPT INTO THE ONE OR MORE HEALTHCARE INSURANCE PLANS OPERATION 313 at AT THE END OF THE SPECIFIED TIME, THE HEALTHCARE INSURANCE PROVIDER WITH THE LOWEST BID PROVIDES THE ONE OR MORE HEALTHCARE INSURANCE PLANS TO THE EMPLOYEES OF THE SMALL BUSINESSES' THAT OPTED INTO THE ONE OR MORE HEALTHCARE INSURANCE PLANS, AT THE LOWEST BID PRICE OPERATION 315, process flow proceeds to EXIT OPERATION 321.

In one embodiment, at EXIT OPERATION 321 process for establishing a healthcare network across small businesses 300 is exited to await new data and/or a new pay period.

In the discussion above, certain aspects of one embodiment include process steps and/or operations and/or instructions described herein for illustrative purposes in a particular order and/or grouping. However, the particular order and/or grouping shown and discussed herein are illustrative only and not limiting. Those of skill in the art will recognize that other orders and/or grouping of the process steps and/or operations and/or instructions are possible and, in some embodiments, one or more of the process steps and/or operations and/or instructions discussed above can be combined and/or deleted. In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein do not limit the scope of the invention as claimed below.

Using either process for establishing a healthcare network across small businesses 200 (FIG. 2) or process for establishing a healthcare network across small businesses 300 (FIG. 3), the employees of multiple enrolled small businesses are grouped together to increase the number of plan participants. Consequently, by their increased numbers, the risk to the healthcare insurance provider is spread over a greater premium base and the collective bargaining power of the employees of the multiple enrolled small businesses allows them to potentially be offered discounts that previously were only available to employees of large companies. In addition, using either process for establishing a healthcare network across small businesses 200 (FIG. 2) or process for establishing a healthcare network across small businesses 300 (FIG. 3), from the healthcare insurance provider's perspective, the actual number of employees of the multiple enrolled small businesses that opt into a given healthcare insurance plan is known in advance. As a result, using either process for establishing a healthcare network across small businesses 200 (FIG. 2) or process for establishing a healthcare network across small businesses 300 (FIG. 3), discounts can be offered based on real data and a known premium base. Consequently, using either process for establishing a healthcare network across small businesses 200 (FIG. 2) or process for establishing a healthcare network across small businesses 300 (FIG. 3), employees of small businesses, small businesses, healthcare insurance providers, and, arguably, society as a whole, are all benefited.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, and/or protocols. Further, the system and/or functionality of the invention may be implemented via various combinations of software and hardware, as described, or entirely in hardware elements. Also, particular divisions of functionality between the various components described herein is merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic and/or algorithm-like descriptions and representations are the means used by those of skill in the art to most effectively and efficiently convey the substance of their work to others of skill in the art. These operations, while described functionally or logically, are understood to be implemented by computer programs and/or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "obtaining" "storing", "offering", "displaying", "enrolling", "providing", "aggregating", "modifying", "accessing", "selecting" etc., refer to the action and processes of a computing system or similar electronic device that manipulates and operates on data represented as physical (electronic) quantities within the computing system memories, resisters, caches or other information storage, transmission or display devices.

Certain aspects of the present invention include process steps or operations and instructions described herein in an algorithmic and/or algorithmic-like form. It should be noted that the process steps and/or operations and instructions of the present invention can be embodied in software, firmware, and/or hardware, and when embodied in software, can be downloaded to reside on and be operated from different platforms used by real time network operating systems.

The present invention also relates to an apparatus or system for performing the operations described herein. This apparatus or system may be specifically constructed for the required purposes, or the apparatus or system can comprise a general purpose system selectively activated or configured/reconfigured by a computer program stored on a computer program product as discussed herein that can be accessed by a computing system or other device.

Those of skill in the art will readily recognize that the algorithms and operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

The present invention is well suited to a wide variety of computer network systems operating over numerous topologies. Within this field, the configuration and management of large networks comprise storage devices and computers that are communicatively coupled to similar and/or dissimilar computers and storage devices over a private network, a LAN, a WAN, a private network, or a public network, such as the Internet.

It should also be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the FIG. s for method and apparatus and/or process or application for establishing a healthcare network across small businesses, discussed herein, are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A system for establishing a healthcare network across businesses comprising:
   one or more computing processors; and
   one or more memories coupled to the one or more computing processors, the one or more memories having stored therein instructions which, when executed by the one or more computing processors, perform a process comprising:
   enrolling two or more businesses in a business employee healthcare insurance network;
   enrolling one or more healthcare insurance providers in the business employee healthcare insurance network;
   offering one or more healthcare insurance plans to the two or more businesses enrolled in the business employee healthcare insurance network at respective initial prices and under respective initial healthcare insurance conditions, resulting in respective offer prices associated with respective ones of the one or more healthcare insurance plans;
   reviewing the offered one or more healthcare insurance plans and the initial price and initial healthcare insurance conditions associated with the one or more healthcare insurance plans;
   opting, during a time frame, at least one of the two or more businesses into participation in at least one of the one or more healthcare insurance plans, a length of the time frame being variable according to when a threshold number of employees opt into the one or more healthcare insurance plans, wherein to participate in a given healthcare plan, a business at least offers that given healthcare plan to its employees wherein opting, during a time frame, at least one of the two or more businesses into participation in at least one of the one or more healthcare insurance plans comprises obligating the opted in one or more businesses to accept coverage under the at least one of the one or more healthcare insurance plans for at least a defined number of the business's employees so long as the offered price associated with the at least one of the one or more healthcare insurance plans is at, or below, a price that was listed at a time the opted in one or more businesses were opted into participation in the at least one of the one or more healthcare insurance plans;
   changing the offer price associated with at least one of the healthcare insurance plans during the time frame, the change being based on profile data associated with employees opted into a given healthcare insurance plan whose offer price is being changed;

determining, following expiration of the time frame, a healthcare insurance provider of the one or more healthcare insurance providers enrolled in the business employee healthcare insurance network that has offered a lowest price for at least one of the one or more healthcare insurance plans, the healthcare insurance provider offering a lowest price being a lowest price healthcare insurance provider; and providing coverage, by the lowest price healthcare insurance provider, to employees of the opted-in businesses, the coverage being under the at least one of the one or more healthcare insurance plans the businesses opted into during the time frame.

2. The system for establishing a healthcare network across businesses of claim 1, wherein;

the one or more healthcare insurance providers enrolled in the business employee healthcare insurance network change the price associated with at least one of the one or more healthcare insurance plans during the time frame based, at least in part, on the number of businesses of the two or more enrolled in the business employee healthcare insurance network that opt into participation in the at least one of the one or more healthcare insurance plans.

3. The system for establishing a healthcare network across businesses of claim 1, wherein;

the one or more healthcare insurance providers enrolled in the business employee healthcare insurance network change the price associated with at least one of the one or more healthcare insurance plans during the time frame based, at least in part, on the number of employees associated with the businesses of the two or more businesses enrolled in the business employee healthcare insurance network that opt into participation in the at least one of the one or more healthcare insurance plans.

4. The system for establishing a healthcare network across businesses of claim 1, wherein;

the one or more healthcare insurance providers enrolled in the business employee healthcare insurance network change the price associated with at least one of the one or more healthcare insurance plans during the time frame based, at least in part, on a competitive response to a price associated with at least one the healthcare insurance plans offered by one or more other healthcare insurance providers enrolled in the business employee healthcare insurance network.

\* \* \* \* \*